(12) United States Patent
Hossainy et al.

(10) Patent No.: US 9,510,976 B2
(45) Date of Patent: Dec. 6, 2016

(54) DEVICES AND METHODS FOR TREATMENT OF THE EUSTACHIAN TUBE AND SINUS CAVITY

(71) Applicant: ABBOTT CARDIOVASCULAR SYSTEMS INC., Santa Clara, CA (US)

(72) Inventors: Syed Hossainy, Hayward, CA (US); Paul Consigny, San Jose, CA (US); Dariush Davalian, San Jose, CA (US); James Su, Sunnyvale, CA (US); Michael Ngo, San Jose, CA (US); Adrain Gale, San Mateo, CA (US); Jesus Magana, Redwood City, CA (US); Mikael Trollsas, San Jose, CA (US); Evan Norton, Wilmette, IL (US); Benjamyn Serna, Gilroy, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/265,343

(22) Filed: Apr. 29, 2014

(65) Prior Publication Data

US 2015/0305943 A1    Oct. 29, 2015

(51) Int. Cl.
*A61F 11/00* (2006.01)
*A61M 25/10* (2013.01)
*A61F 2/915* (2013.01)
(Continued)

(52) U.S. Cl.
CPC .............. *A61F 11/002* (2013.01); *A61F 2/915* (2013.01); *A61F 2/958* (2013.01); *A61M 25/10* (2013.01); *A61M 29/02* (2013.01); *A61F 2002/91575* (2013.01); *A61F 2230/0067* (2013.01); *A61F 2250/005* (2013.01); *A61F 2250/0018* (2013.01); *A61F 2250/0026* (2013.01); *A61F 2250/0046* (2013.01); *A61F 2250/0048* (2013.01); *A61F 2250/0082* (2013.01);
(Continued)

(58) Field of Classification Search
CPC .......... A61F 2/82; A61F 2/89; A61F 11/002; A61F 11/004; A61B 17/24
See application file for complete search history.

(56) References Cited

U.S. PATENT DOCUMENTS

| 5,234,456 A | 8/1993 | Silvestrini |
| 5,437,290 A | 8/1995 | Bolger et al. |

(Continued)

FOREIGN PATENT DOCUMENTS

| CA | 2 370 180 A1 | 10/2000 |
| DE | 10 2010 043332 B3 | 10/2011 |

(Continued)

OTHER PUBLICATIONS

International Search Report and Written Opinion of the International Searching Authority, Appln. No. PCT/US2015/027939 mailed Nov. 16, 2015, 18 pages.

*Primary Examiner* — Thomas J Sweet
*Assistant Examiner* — Daniel Bissing
(74) *Attorney, Agent, or Firm* — Squire Patton Boggs (US) LLP

(57) ABSTRACT

A polymeric stent can be implanted for treatment of the Eustachian tube. The stent can be designed to have length-dependent radial strength to allow it to stay within the Eustachian tube and to allow normal closing and opening of the Eustachian tube. A balloon can be used to implant the stent, and the balloon can be coated with a therapeutic agent. A coated balloon can also be used to transfer therapeutic agents to the sinus cavity during a balloon sinus dilation procedure.

11 Claims, 6 Drawing Sheets

(51) Int. Cl.
*A61F 2/958* (2013.01)
*A61M 29/02* (2006.01)
(52) U.S. Cl.
CPC ............... *A61M 2025/105* (2013.01); *A61M 2025/1059* (2013.01); *A61M 2210/0675* (2013.01)

(56) References Cited

U.S. PATENT DOCUMENTS

| | | | |
|---|---|---|---|
| 5,575,818 A | 11/1996 | Pinchuk | |
| 5,582,171 A | 12/1996 | Chornenky et al. | |
| 6,589,286 B1 * | 7/2003 | Litner | A61F 11/002 604/8 |
| 7,476,245 B2 | 1/2009 | Abbate | |
| 7,532,920 B1 | 5/2009 | Ainsworth et al. | |
| 7,833,282 B2 | 11/2010 | Mandpe | |
| 8,002,817 B2 | 8/2011 | Limon | |
| 8,147,545 B2 | 4/2012 | Avior | |
| 8,560,048 B2 | 10/2013 | Eberle et al. | |
| 8,579,973 B2 | 11/2013 | Avior | |
| 2003/0070676 A1 * | 4/2003 | Cooper | A61B 8/12 128/200.24 |
| 2005/0240147 A1 | 10/2005 | Makower et al. | |
| 2006/0089627 A1 * | 4/2006 | Burnett | A61B 17/12099 606/1 |
| 2006/0095066 A1 | 5/2006 | Chang et al. | |
| 2006/0135985 A1 | 6/2006 | Cox et al. | |
| 2007/0207186 A1 | 9/2007 | Scanlon et al. | |
| 2007/0208301 A1 | 9/2007 | Evard et al. | |
| 2007/0283552 A1 | 12/2007 | Gale et al. | |
| 2008/0103584 A1 * | 5/2008 | Su | A61F 2/91 623/1.16 |
| 2008/0132990 A1 | 6/2008 | Richardson | |
| 2008/0262468 A1 | 10/2008 | Clifford et al. | |
| 2008/0262508 A1 | 10/2008 | Clifford et al. | |
| 2008/0262509 A1 | 10/2008 | Clifford et al. | |
| 2008/0262510 A1 | 10/2008 | Clifford | |
| 2009/0158852 A1 | 6/2009 | Paul et al. | |
| 2009/0163890 A1 | 6/2009 | Clifford et al. | |
| 2010/0021519 A1 | 1/2010 | Shenoy | |
| 2010/0125326 A1 | 5/2010 | Kalstad et al. | |
| 2010/0198191 A1 | 8/2010 | Clifford et al. | |
| 2011/0035927 A1 | 2/2011 | Griffin et al. | |
| 2011/0066222 A1 | 3/2011 | Wang et al. | |
| 2011/0184507 A1 | 7/2011 | Fischer, Jr. et al. | |
| 2013/0253477 A1 | 9/2013 | Wang et al. | |
| 2013/0274715 A1 | 10/2013 | Chan et al. | |
| 2013/0331927 A1 * | 12/2013 | Zheng | A61F 2/82 623/1.19 |
| 2014/0088703 A1 * | 3/2014 | Schuessler | A61F 2/12 623/8 |

FOREIGN PATENT DOCUMENTS

| | | |
|---|---|---|
| EP | 0 447 719 A1 | 9/1991 |
| WO | WO 01/32148 | 5/2001 |
| WO | WO 2013/130464 A1 | 9/2013 |
| WO | WO 2015/168087 | 5/2015 |

* cited by examiner

DEVICES AND METHODS FOR TREATMENT OF THE EUSTACHIAN TUBE AND SINUS CAVITY

FIELD

This application relates generally to medical devices and methods and, more particularly, to medical devices and methods for the Eustachian tube and/or the sinus cavity.

INCORPORATION BY REFERENCE

All publications and patent applications mentioned in this specification are herein incorporated by reference to the same extent as if each individual publication or patent application was specifically and individually indicated to be incorporated by reference.

BACKGROUND

As shown in FIG. 19, the ear 900 can be divided into three parts: the external ear, the middle ear 902, and the inner ear 904. The external ear includes the visible part of the ear (the pinna) and the ear canal 906. The middle ear 902 is an air-filled space behind the tympanic membrane 908, also known as the ear drum. The middle ear 902 contains small bones, known as the ossicles. The inner ear 904 contains the sensory organs for hearing (the cochlea) and balance (the semicircular canals).

The Eustachian tube 910 is a narrow tube that connects the middle ear 902 to the back of the nose. In adults, the Eustachian tube 910 is about 35 mm in length, is bony along one third of its length nearest the ear drum 908 and is cartilaginous along the remaining two thirds of its length nearest the opening 912 to the nasopharynx cavity 914. The opening 912 can be about 1 mm in diameter. The opening 912 can be reached from the nose or the mouth.

The Eustachian tube 910 is normally closed, but it can open periodically, such as when swallowing or yawning. In this way, the Eustachian tube 910 acts like a pressure-equalizing valve for the middle ear. The Eustachian tube 910 also serves to drain mucus produced by the lining of the middle ear 902. Infections or allergies can cause the Eustachian tube 910 to become swollen and lead to Eustachian tube dysfunction (ETD), which is a common problem for both children and adults. When the Eustachian tube 910 is obstructed, due to anatomical or inflammatory reasons, the middle ear 092 is not able to equalize pressure, which can lead to negative pressure and fluid build-up. ETD can lead to many ontological problems, such as chronic otitis media, refraction of the tympanic membrane, hearing loss, and cholesteatoma.

According, there is a continuing need for devices and methods for treating the Eustachian tube.

In addition, functional endoscopic sinus surgery (FESS) is performed by ear, nose, and throat (ENT) surgeons to treat patients with chronic sinusitis. FESS can improve sinus drainage by enlarging drainage pathways, which is often achieved through surgical removal of nasal structures and expansion of the sinus ostia, the natural openings of the sinus. While FESS involves removal of some existing structures, ENT surgeons work to preserve the lining of the sinus, called mucosa, because it plays an important role in drainage. Potential risks to undergoing traditional sinus surgery include but not limited to excessive bleeding, cerebrospinal fluid leak, intraorbital complications, and a failure to resolve sinus conditions.

Topical corticosteroids are commonly prescribed for chronic sinusitis (or rhinosinusitis), which is the inflammation of the paranasal sinuses. Oral steroid medications are also prescribed routinely in rhinology-oriented practices for patients with nasal polyps or chronic hyperplastic rhinosinusitis. However, the use of systemic steroids has the potential for steroid-related complications, such as aseptic necrosis of the femoral head, calcium demineralization, posterior cataract formation, mood disorders, and difficulty in controlling blood glucose levels in diabetic patients.

Accordingly, there is a continuing need for devices and methods for treating the sinuses.

SUMMARY

Described herein are devices and methods for treating a Eustachian tube or a sinus cavity.

In various aspects, a polymeric stent for treating the Eustachian tube comprises a tubular scaffold configured for implantation in the Eustachian tube. The tubular scaffold has a polymer substrate. The tubular scaffold includes a proximal segment and a distal segment. The proximal segment includes radially deformable rings. The distal segment includes radially deformable rings having a greater radial strength than the radially deformable rings of the proximal segment.

In various aspects, a system for delivering a stent in the Eustachian tube comprises a catheter including a body and a balloon at the end of the body. The balloon is configured to carry a stent for delivery through a nasopharynx cavity and into a Eustachian tube of a patient.

In various aspects, a catheter for treating the Eustachian tube or the sinus cavity comprises a body, a balloon at the end of the body, and a coating on the balloon. The balloon is configured to pass into a sinus cavity or into a Eustachian tube of a patient. The coating includes at least one therapeutic agent.

In various aspects, a method of treating the Eustachian tube with a stent comprises placing a stent in a Eustachian tube of a patient.

In various aspects, a method of treating a Eustachian tube or sinus cavity with a balloon comprises inflating a balloon in a Eustachian tube or a sinus cavity of a patient, and allowing at least one therapeutic agent to transfer from the balloon to a wall of the Eustachian tube or the sinus cavity.

The features and advantages of the invention will be more readily understood from the following detailed description which should be read in conjunction with the accompanying drawings.

DETAILED DESCRIPTION OF EXEMPLARY EMBODIMENTS

The terms "biodegradable," "bioresorbable," "bioabsorbable," and "bioerodable" are used interchangeably herein and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, by hydrolysis and metabolic processes.

The term "biostable" refers to polymers that are not biodegradable.

Figure 1:
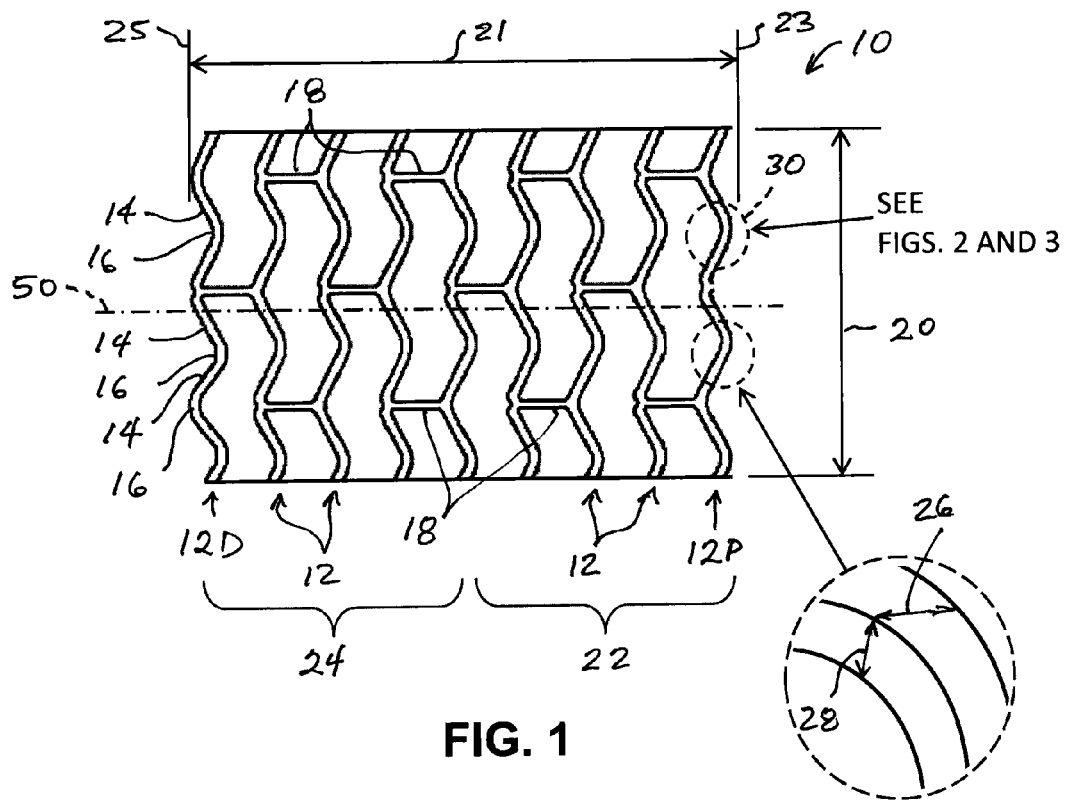
FIG. 1 is a plan view showing an exemplary polymeric stent for use in the Eustachian tube.

Referring now in more detail to the exemplary drawings for purposes of illustrating embodiments, wherein like reference numerals designate corresponding or like elements among the several views, there is shown in FIG. 1 exemplary stent 10 configured to be implanted in the Eustachian tube. Stent 10 includes a plurality of radially deformable rings 12 which are arranged axially to form a tubular scaffold. Each ring 12 comprising a series of ring struts 14. Each ring strut 14 is connected by hinge 16 to adjacent ring strut 14. Each ring 12 is connected by links 18 to adjacent ring 12. Rings 12 at opposite ends of stent 10 are further identified by the letters "P" and "D". All hinges 16 are configured to bend during crimping and deployment of stent 10. During crimping and deployment, hinges 16 mechanically deform to allow a change in overall outer diameter 20 of each ring 12.

Figure 13:
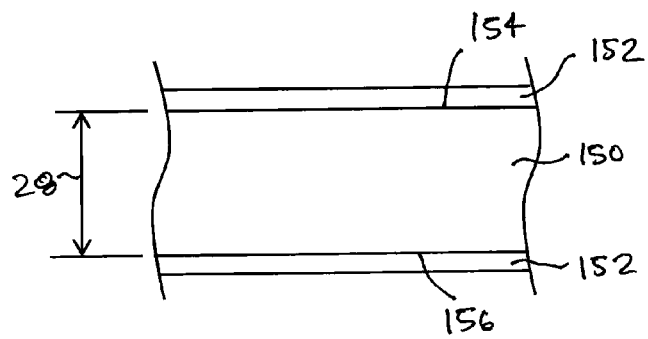
FIG. 13 is a section view of a portion of a stent, showing a polymer substrate and a coating.

Ring struts 14, hinges 16, and links 18 are constructed of polymer substrate 150 (see, for example, FIG. 13). The strength and elasticity of the polymer substrate allows stent 10 to be crimped to a reduced configuration, and then deployed to an enlarged configuration so that it makes contact with surrounding tissue. Contact with surrounding tissue allows the stent to remain in place within the Eustachian tube and allows for optional delivery of a therapeutic agent from the stent directly to the tissue.

Although only nine rings 12 are illustrated in FIG. 1, it is to be understood that stent 10 can have a greater number of rings 12 arranged axially along the overall length of stent 10. The number of rings 12 may depend upon the desired overall length 21 of stent 10. The overall length of stent 10 can be selected based on the region of the Eustachian tube which is to be treated. It is to be understood that FIG. 1 is a simplified view of rings 12. Each ring 12 forms a loop that encircles central axis 50.

Stent 10 is illustrated with W-shaped closed cells arranged in an offset brick pattern. It is to be understood that that the stent pattern is not limited to what is depicted. The stent pattern refers to the arrangement, and orientation of rings and of the various struts, hinges, and links For example, the stent can have diamond-shaped closed cells or V-shaped closed cells. The stent can have any of the stent patterns described in U.S. Pat. Nos. 7,476,245 and 8,002,817. The stent can have virtually any stent pattern suitable for a polymer substrate.

In an exemplary embodiment, overall length 21 matches the length of the bony part of the Eustachian tube. In adult persons, the length of the bony part is approximately 10 mm, so overall length 21 can be from 7 mm to 14 mm, or from 11 mm to 14 mm, or about 10 mm.

When used as a modifier preceding a numerical value, the term "about" means plus or minus 10% of the numerical value. For example, "about 10 mm" means from 9 mm to 11 mm, and "about 20 mm" means from 18 mm to 22 mm.

In an exemplary embodiment, overall length 21 matches the length of the cartilaginous part of the Eustachian tube. In adult persons, the length of the cartilaginous part is approximately 20 mm, so overall length 21 can be from 17 mm to 25 mm, or from 18 mm to 23 mm, or about 20 mm.

In an exemplary embodiment, overall length 21 matches the length of the bony part plus the cartilaginous part of the Eustachian tube. For example, overall length 21 can be from about 12 mm to about 38 mm, or 31 mm to 38 mm, or about 35 mm.

In any of the above embodiments herein, overall outer diameter 20 of each ring 12 is from about 3 mm to about 4 mm before crimping of stent 10 and/or after deployment of stent 10.

In an exemplary embodiment, overall length 21 is about 10 mm, and stent 10 is centered in the middle segment of the cartilaginous segment of the Eustachian tube. With a Eustachian tube that is about 35 mm in length in most adults, the cartilaginous segment can be about 20 mm in length. With this centered placement of stent 10 in a cartilaginous segment of about 20 mm, stent 10 would not extend into a 5 mm segment of the cartilaginous segment that is closest to the opening 912 (FIG. 19) of the Eustachian tube. That 5 mm segment would be free to open and close without any risk of interference from stent 10.

In an exemplary embodiment, overall length 21 is about 10 mm and distal edge 25 of stent 10 is placed at the junction between the bony and cartilaginous segments of the Eustachian tube that is about 35 mm in length. With this off-center placement of stent 10 in a cartilaginous segment of about 20 mm, stent 10 would not extend into a 10 mm segment of the cartilaginous segment that is closest to the opening 912 (FIG. 19) of the Eustachian tube. That 10 mm segment would be free to open and close without any risk of interference from stent 10.

As shown in FIG. 1, stent 10 includes proximal segment 22 and distal segment 24. Proximal segment 22 abuts distal segment 24. Proximal segment 22 begins at end ring 12P at one end (proximal end 23) of stent 10. Distal segment 24 begins at end ring 12D at the opposite end (distal end 25) of stent 10.

As used herein, the term "proximal segment" is the portion of stent 10 that is intended to be closest to the opening 912 (FIG. 19) of the Eustachian tube when stent 10 is implanted. The term "distal segment" is the portion of stent 10 that is intended to be closest to the tympanic membrane 908 (FIG. 19) when stent 10 is implanted.

In some embodiments, proximal segment 22 and distal segment 24 are each half of the overall length 21 of stent 10. For example, proximal segment 22 can be about 5 mm in length and distal segment can be about 5 mm in length. As a further example, proximal segment 22 can be about 10 mm in length and distal segment can be about 10 mm in length.

In alternative embodiments, proximal segment 22 and distal segment 24 are unequal in length.

Keeping the Eustachian tube open all the time can cause complications. For example, patulous Eustachian tube is a disorder where the Eustachian tube stays open and does not close normally. When the Eustachian tube stays open, the person experiences autophony, the hearing of sounds generated by the body, such as breathing, one's own voice, and heartbeat.

Thus, in some embodiments, distal segment 24 has a greater radial strength than proximal segment 22. Lower radial strength of proximal segment 22 can encourage natural opening and closing of portions of the cartilaginous segment of the Eustachian tube. As used herein, radial strength refers to the ability of rings 12 to resist radially inward compression forces that can reduce the diameter of the rings 12. For example, rings 12 within distal segment 24 can be configured to have a greater resistance to radially inward compression forces than rings 12 within proximal segment 22. This length-dependent radial strength can be accomplished by creating discontinuities 27 in the rings 12. For example, discontinuities 27 can be formed in one or more rings 12 within proximal segment 22 while discontinuities 27 are absent from all rings 12 within distal segment 24.

Figure 2:
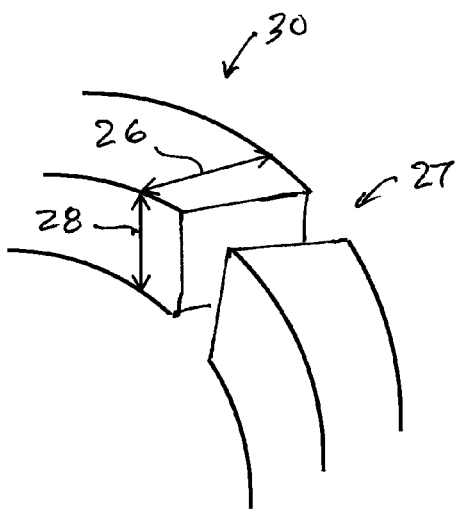
FIGS. 2 and 3 are detail views showing an exemplary portion of the stent.

As shown in FIG. 2, exemplary discontinuity 27 can be in the form of a full cut that passes completely across full width 26 and full thickness 28 of portion 30 of ring 12. As used herein, the term "thickness" refers to a dimension in a radial direction that is perpendicular to central axis 50 of the stent.

Figure 3:
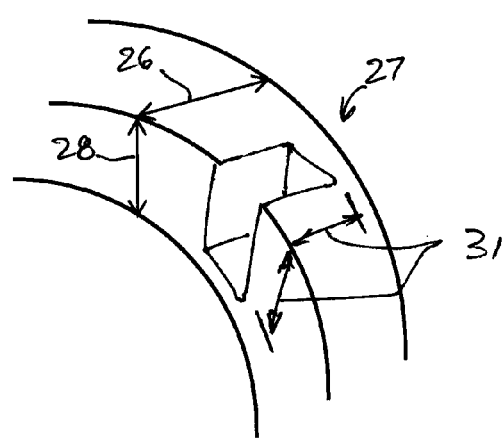

Exemplary discontinuity 27 can be a partial cut. As used herein, a partial cut is a cut that passes only partially across any one or both of full width 26 and full thickness 28. For example, as shown in FIG. 3, exemplary discontinuity 27 can be in the form of a partial cut that passes partially across full width 26 and full thickness 28. Alternatively, the partial cut can pass completely across full width 26 but does not pass completely across full thickness 28. Alternatively, the partial cut can pass completely across full thickness 28 but does not pass completely across full width 26. Depth 31 of the cut can be sufficient to enable ring 12 to break across full width 26 and full thickness 28 at discontinuity 27 during crimping of stent 10 onto a delivery catheter and/or during expansion of stent 10 when deploying and implanting stent 10 in the Eustachian tube. For example, depth 31 of a partial cut can be at least 30%, at least 50%, or at least 80% of full width 26 and/or full thickness 28.

In some embodiments, discontinuities 27 in the form of full or partial cuts are formed at the time when rings 12 are created during an in injection molding process or a casting process. In such cases, it may not be necessary to remove or cut in material from the polymer substrate in order to form discontinuity 27.

Alternatively, discontinuities 27 in the form of full or partial cuts are formed after rings 12 are created. In such cases, parts of the polymer substrate can be removed or cut in order to form discontinuity 27. Parts can be removed or cut using a laser device or mechanical knife.

Portion 30 illustrated in FIGS. 2 and 3 can be one of the ring struts 14 or one of the hinges 16 of a ring. Although only one ring 12 of proximal segment 22 is illustrated as having a single discontinuity 27, it is to be understood that all or any number of the rings of stent 10 can have one or more discontinuities. For example, all rings 12 of proximal segment 22 can have discontinuities 27, while discontinuities are absent from all rings 12 of distal segment 24. The number of discontinuities 27 can decrease with increasing distance from proximal end 23. For example, end ring 12P of proximal segment 22 can have a greater number of discontinuities 27 than another ring 12 of proximal segment 22. As a further example, there can be a total of three discontinuities 27 in end ring 12P while there is only discontinuity 27 in the ring adjacent to distal segment 24.

In some embodiments, distal segment 24 is narrower than proximal segment 22 to accommodate to some extent the natural shape of the Eustachian tube. In this context, the term "narrower" means that one or more rings 12 within distal segment 24 have a smaller outer diameter 20 than one or more rings 12 within proximal segment 22. This difference in outer diameter 20 exists in stent 10 before stent 10 is crimped onto a delivery catheter and after stent 10 is deployed in the Eustachian tube. A narrower proximal segment 22 can encourage natural opening and closing of the Eustachian tube.

Figure 4A:
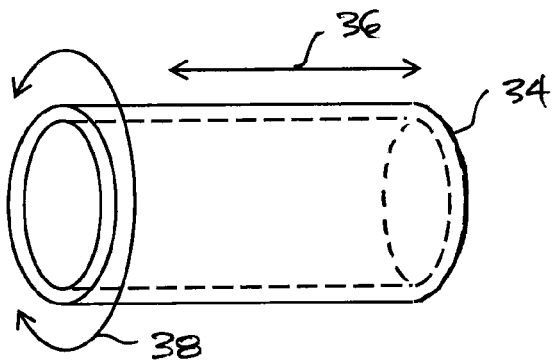
FIG. 4A is an isometric view showing an exemplary precursor tube which can be used to make the tube of FIG. 4B.
Figure 4B:
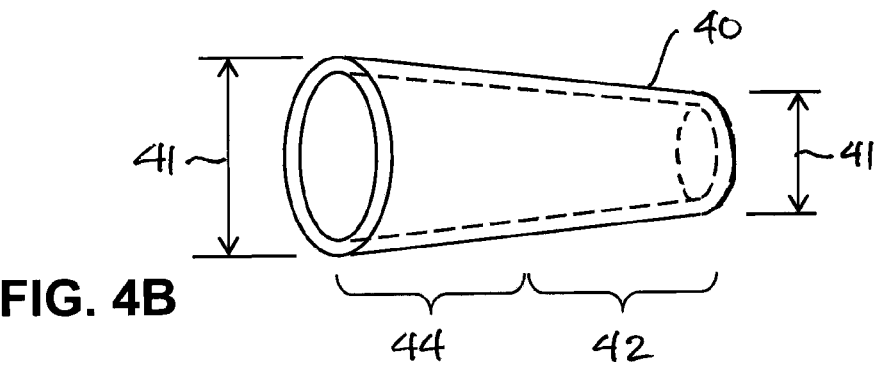
FIGS. 4B and 4C are an isometric views showing exemplary tubes which can be used to make a stent.

In some embodiments, as shown in FIG. 4B, stent 10 can be made from tube 40 which has a greater outer diameter 41 at one end as compared to the opposite end. Tube segment 42 with the smaller outer diameter will eventually become proximal segment 22 of stent 10, while tube segment 44 with the larger outer diameter will eventually become distal segment 24 of stent 10. A cutting tool, such as a laser device or a mechanical knife, can be used to cut material away from tube 40 to form rings 12 (with or without discontinuities 27) of proximal and distal segments 22 and 24. Cutting using a laser can be performed as described in U.S. Publication No. 2007/0283552 A1.

Tube 40 can be formed by extruding polymer substrate material out of a die to form a precursor tube having a uniform outer diameter. Exemplary precursor tube 34 is shown in FIG. 4A. Next, precursor tube 34 can be radially expanded by a blow molding process which increases the internal air pressure within the precursor tube while the precursor tube is heated. Blow molding can be performed as described in U.S. Publication No. 2011/0066222 A1. The internal pressure, temperature, and/or other parameter can be adjusted during the blow molding process to achieve a tube having a length-dependent outer diameter, such as tube 40 in FIG. 4B. Before blow molding, the polymer molecule chains in precursor tube 34 can have orientations that are preferentially aligned in axial direction 36. The preferential axial orientation can arise from the extrusion process. Radial expansion of the precursor tube, such as during a blow molding process, will induce the polymer molecule chains to have a preferential orientation that is less axial and more aligned in circumferential direction 38. As used herein, "less axial" encompasses a preferential orientation of polymer molecule that is any one of circumferential (in the direction of arrow 38), mostly circumferential, partially circumferential, and partially axial (in the direction of arrow 36). Orientation of polymer molecule chains can be determined by polarized light microscopy.

Alignment in circumferential direction 38 is associated with greater radial strength. Due to less radial expansion of precursor tube 34 (FIG. 4A) to form tube segment 42 (FIG. 4B), the polymer molecule chains in rings 12 within proximal segment 22 of stent 10 can retain a preferentially axial orientation. In comparison, due to greater radial expansion of precursor tube 34 (FIG. 4A) to form tube segment 44 (FIG. 4B), the polymer molecule chains in rings 12 within distal segment 24 of stent 10 can be induced to have a preferentially circumferential orientation that increases the strength of ring struts 14 in circumferential direction 38 and enables rings 12 within distal segment 24 to have greater radial strength than rings 12 within proximal segment 22.

In some embodiments, rings 12 can be formed, such as by cutting tube 40, so that full width 26 of rings 12 within distal segment 44 is greater than full width 26 of rings 12 within proximal segment 42. This difference in full width 26 among rings 12 can enable distal segment 24 to have greater radial strength than proximal segment 22.

Figure 4C:
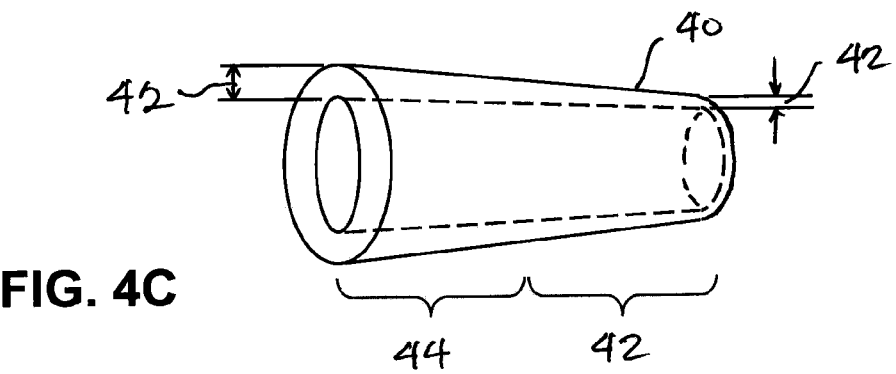

As shown in FIG. 4C, tube 40 can be formed, such as by injection molding or casting or extrusion, so that wall thickness 42 of tube 40 is greater at tube segment 44 than at tube segment 42. Rings 12 can be formed, such as by cutting tube 40, so that full thickness 28 of rings 12 within distal segment 44 is greater than full thickness 28 of rings 12 within proximal segment 42. This difference in full thickness 28 among rings 12 can enable distal segment 24 to have greater radial strength than proximal segment 22.

Any of the ways for enabling distal segment 24 to have greater radial strength than proximal segment 22, as described above, can be combined to construct stent 10. For example, as compared to rings 12 within proximal segment 22, rings 12 within distal segment 24 can have any one or a combination of the following features: (1) lesser number or total absence of discontinuities 27, (2) polymer molecule chains having a preferential orientation that is less axial, (3) full widths 26 that are greater in size, and (4) full thicknesses 28 that are greater size. Any one or a combination of features (1), (3) and (4) can be achieved with three-dimensional printing methods in which an additive process lays down or bonds together successive layers to form the desired shape for tube 40 or stent 10.

Figure 5:
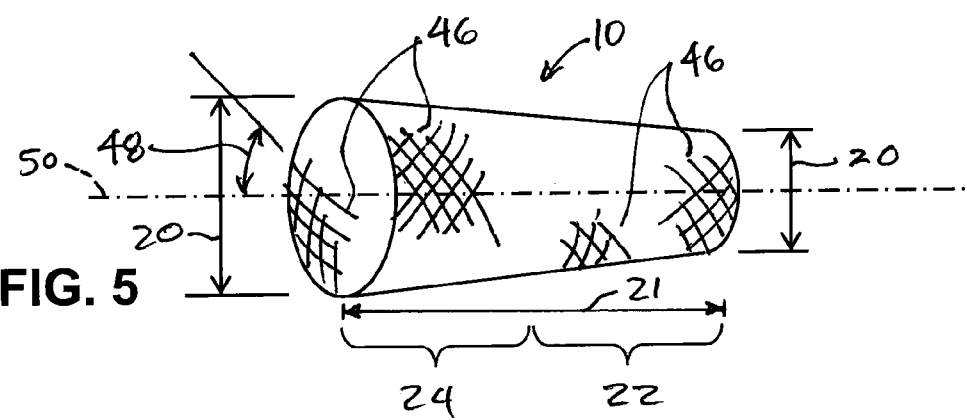
FIG. 5 is an isometric view showing an exemplary stent.

As shown in FIG. 5, stent 10 can also be a tubular scaffold formed from a tubular braid of filaments 46. Each filament 46 has polymer substrate 150 (see, for example, FIG. 13). Variations along overall length 21 of braid characteristics of filaments 46 enable stent 10 to have distal segment 24 that has a greater radial strength than proximal segment 22. Braid characteristics include braid angle, outer diameter 20, and filament density. The braid angle is acute angle 48 measured from filament 46 to a line parallel to central axis 50. For example, distal segment 24 can have greater braid angles than proximal segment 22. Filament density can be in terms of weight of filaments 46 per unit area of stent 10 or weight of filaments 46 per unit length of stent 10. For example, distal segment 24 can have greater filament density than proximal segment 22.

It will be appreciated from the forgoing descriptions that stent 10 can have axially varying load bearing mechanical properties along the length of the Eustachian tube. This applies to stent 10 of FIGS. 1-3 and 5 and to stents made from tubes 40 of FIGS. 4B and 4C. The axial variability can be introduced by any one or a combination of parameters, such as: (a) polymer backbone architecture; (b) polymer molecular weight, including random versus block; (c) polymer processing for different degree of chain orientation in the axial versus circumferential directions; (d) dimension of the strut width and thickness; and (e) introduction of varying number of discontinuities per unit length.

For example, in a stent according to FIGS. 1-3, axial variability in load bearing mechanical properties can arise from a varying number of discontinuities along the axial length of the stent. For example, proximal segment 22 of the stent can have a greater number of discontinuities 27 than distal segment 24 so that distal segment 24 has greater radial strength than proximal segment 22.

For example, in a stent made from tube 40 in FIG. 4B, axial variability in load bearing mechanical properties can arise from processing for different degree of polymer chain orientation in the axial direction versus circumferential direction. For example, proximal segment 22 of the stent can have a polymer substrate in which the preferential polymer chain orientation is more axial than the preferential polymer chain orientation of the polymer substrate of the distal segment 24, so that distal segment 24 has greater radial strength than proximal segment 22.

For example, in the stent made from tube 40 in FIG. 4C, axial variability in load bearing mechanical properties can arise from a dimension, such as width and/or thickness, of a stent structural element, such as struts 14, hinges 16, and links 18. For example, proximal segment 22 of the stent can have struts 14, hinges 16, and/or links 18 which are smaller in width and/or thickness than struts 14, hinges 16, and/or links 18 of distal segment 24, so that distal segment 24 has greater radial strength than proximal segment 22.

Axial variability in load bearing mechanical properties can also be introduced in the stent by having a variation the molecular weight of the polymer substrate, which may be a random copolymer and a block copolymer. For example, proximal segment 22 of the stent can have a substrate made of a first polymer, and distal segment 24 of the stent can have a substrate made of a second polymer that is greater in molecular weight than the first polymer, so that distal segment 24 has greater radial strength than proximal segment 22. In some embodiments, the first polymer can be PLLA (or other lactic acid polymer or a polymer based on PLA) having a first molecular weight and the second polymer can be PLLA (or the same lactic acid polymer or the same polymer based on PLA) having a second molecular weight greater than the first molecular weight. Alternatively, the first polymer and the second polymer can have a different chemical composition.

Axial variability in load bearing mechanical properties can also be introduced in the stent by a variation in the polymer backbone architecture along the axial length of the stent. For example, proximal segment 22 of the stent can have a first polymer backbone architecture, and distal segment 24 of the stent can have a second polymer backbone architecture that provides distal segment 24 with greater radial strength than proximal segment 22.

The polymer backbone architecture may refer to the way in which components of a polymer are organized and/or may refer to the proportion of components of the polymer. For example, proximal segment 22 of the stent can have a polymer substrate made of a first lactic acid polymer, and distal segment 24 of the stent can have a polymer substrate made of a second lactic acid polymer that provides distal segment 24 with greater radial strength than proximal segment 22. The first and second lactic acid polymers can both be PLLA-co-PCL (a copolymer of poly(L-lactide) and poly (caprolactone)) but with different architecture. The proportion of PLLA is greater in the second lactic acid polymer (used for distal segment 24) than in the first lactic acid polymer (used in proximal segment 22). The proportion of PCL is lower in the second lactic acid polymer (used for distal segment 24) than in the first lactic acid polymer (used in proximal segment 22). PCL has a lower elastic modulus than PLLA, which results in distal segment 24 having greater radial strength than proximal segment 22.

In the above example, PLLA is referred to as the base component, and PCL is referred to as the dopant. PCL can be replaced with any other suitable dopant having a lower elastic modulus than the base component. For example, the dopant can be poly(D-lactide) (PDLA), which has a lower elastic modulus than PLLA. Also, PLLA can be replaced with other suitable base components. The base component need not be bioabsorbable. For example, the base component can be a biostable polymer such as polyurethanes (SPU), polypropylene (PP), and polyetherimide block copolymers (e.g., PEBAX (R)).

As used herein, the "base component" by definition has a greater elastic modulus than the "dopant." The proportion of any base component (e.g., PLLA or other) in the polymer used to make distal segment 24 (which could be implanted in the bony segment of the Eustachian tube) can within the range of about 50% to about 95%, with the dopant (e.g., PCL, PDLA, or other) having the remaining percentage. The proportion of the base component can instead be in the range of about 60% to about 95%, or about 70% to about 95%. In addition or alternatively, the proportion of any dopant (e.g., PCL, PDLA, or other) in the polymer used to the proximal segment 22 (which could be implanted in the cartilaginous segment of the Eustachian tube) can be within the range of about 50% to about 95%, with the base component (e.g., PLLA or other) having the remaining percentage. The proportion of the dopant can instead be in the range of about 60% to about 95%, or about 70% to about 95%.

In addition or alternatively, the polymers used to make distal segment 24 (which could be implanted in the bony segment of the Eustachian tube) and the proximal segment 22 (which could be implanted in the cartilaginous segment of the Eustachian tube) can have the exemplary characteristics shown in TABLE I. The characteristics of polymer substrate 150 are in terms of Tm (melt temperature), Tg (glass transition temperature) and percent crystallinity. Distal segment 24 could have a greater radial strength than proximal segment 22 when polymer substrate 150 of distal segment 24 has one or more of the following three properties relative to polymer substrate 150 of proximal segment 22: (1) greater Tm, (2) greater Tg, and (2) greater percent crystallinity.

TABLE I

|  | Tm | Tg | Percent Crystallinity |
|---|---|---|---|
| Polymer substrate 150 of distal segment 24 | 150° C. to 250° C. | 45° C. to 100° C. | 25% to 70% |
| Polymer substrate 150 of proximal segment 22 | 50° C. to 250° C. (* see note) | −60° C. to 65° | 0% to 70% |

* Note:
No Tm if polymer substrate 150 is an amorphous polymer.

Proximal segment 22 and distal segment 24 can be formed separately to achieve the desired polymer characteristics or backbone architecture for each segment. After each segment is formed independently, proximal segment 22 and distal segment 24 are joined together such as with the use of an adhesive, heat, or interlocking structures.

Alternatively, proximal segment 22 and distal segment 24 can be formed simultaneously to form a unitary structure having no structural seam or joint between the two segments while each segment has its own polymer characteristics or backbone architecture. This can be accomplished, for example, by a three-dimensional printing process in which particles of polymer substrate 150 for proximal segment 22 are deposited on one area of a three-dimensional print bed, and particles of polymer substrate 150 for distal segment 24 are deposited on an adjacent area of the three-dimensional print bed. During the bonding process, particles for proximal segment 22 are bonded to each other and are also bonded to adjacent particles for distal segment 24.

Figure 6:
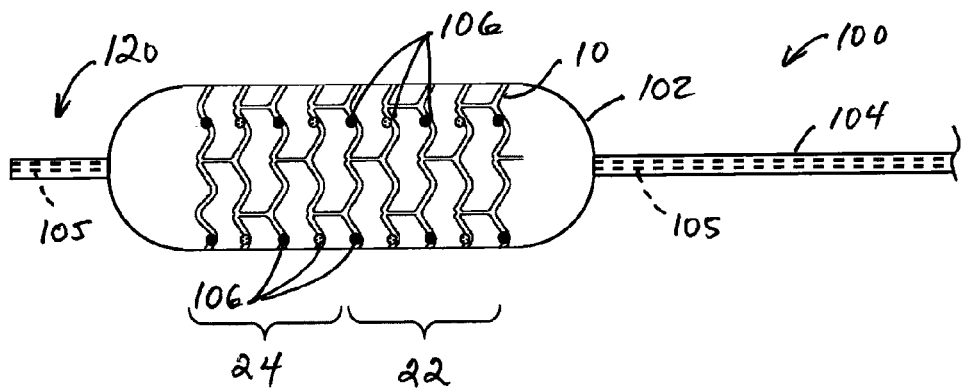
FIG. 6 is a plan view showing a stent on an exemplary delivery catheter.

As shown in FIG. 6, exemplary delivery catheter 100 can be used to carry and deploy stent 10 in the Eustachian tube. Delivery catheter 100 can be inserted into the Eustachian tube via the nasopharynx cavity 914 (see FIG. 19). The total axial length of delivery catheter 100 can be 20 cm to 50 cm. Catheter 100 includes balloon 102 at the end of catheter body 104. While balloon 102 is in a folded state, stent 10 can be crimped to a reduced diameter onto balloon 102. Balloon 102 is inflated to deploy stent 10 to an enlarged diameter after delivery catheter 100 is inserted into the Eustachian tube and after it has been determined that stent 10 is positioned at the desired region of the Eustachian tube.

Stent 10 can include optically visible marks to help determine whether stent 10 is at the desired region of the Eustachian tube. For example, stent 10 can include stent marks 106, which are depicted schematically as round dots. Stent marks 106 are periodically spaced apart from each other along the length of stent 10. Since the length of the Eustachian tube in adults is fairly constant and about 35 mm in total length (the bony segment being about one third of the total length and the cartilaginous segment being about two thirds of the total length) stent marks 106 can function like a visual depth gauge that can indicate to a physician the position of stent 10.

Stent marks 106 can be applied before or after stent 10 is crimped onto a delivery device. When applied after stent 10 is crimped, each stent mark 106 can be in the form of a band that extends around the entire outer circumference of stent 10. Application of each stent mark 106 can be precisely controlled such that each band indicates a predefined length of stent 10. For example, one stent mark 106 can indicate a length of the stent as being 2 mm, and the next stent mark can indicate a length of the stent as being 4 mm.

Stent marks 106 can include a thin material that is coated on the polymer substrate of the stent. The thin material can have a color that contrasts with areas of stent 10 which surround stent marks 106. For example, stent marks 106 can be black or have color that is darker than a polymer substrate that is optically translucent. Additionally or alternatively, stent marks 106 can include an etched mark on the surface of the polymer substrate. The etched mark, which can be produced by a laser or other method, can be opaque and have a level of opacity that makes it readily visible and distinguishable from areas of stent 10 which surround stent marks 106. For example, stent marks 106 which are etched can create a spot or region that has a greater opacity than a polymer substrate that is optically translucent.

Stent marks 106 are sized to be readily visible and distinguishable from areas of stent 10 which surround stent marks 106 when viewed using an endoscope or other imaging device within the Eustachian tube. For example, stent marks 106 can have a size that is at least 0.2 mm, about 0.2 mm, at least 0.3 mm, about 0.3 mm, at least 0.4 mm, or about 0.4 mm. Additionally or alternatively, each stent mark 106 can have the shape of a symbol (such as a circle, square, rectangle, alphanumeric character, or combination thereof) that distinguishes the stent mark from adjacent stent marks.

Any of the stent marks described above can be equally spaced apart from each other. For example, stent marks 106 can be placed on each ring 12 of stent 10. As a further example, stent marks 106 can be placed on each ring 12 and each link 18 of stent 10.

Figure 7:
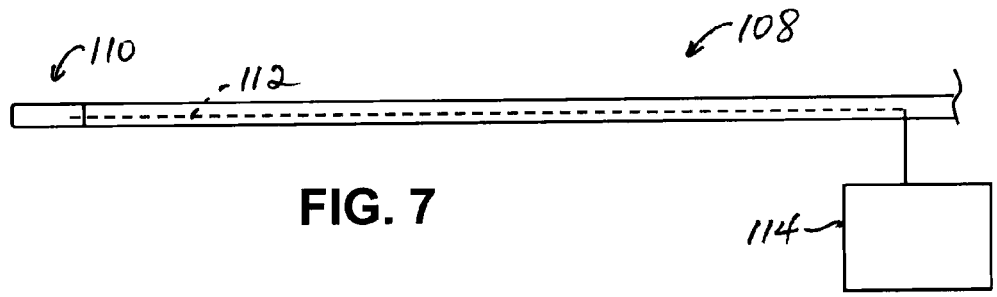
FIG. 7 is a plan view showing an exemplary gauge catheter.

In addition or as an alternative to stent marks 106, a method for implanting stent 10 can include the following sequence of steps to minimize the risk of contact with the tympanic membrane. Gauge catheter 108, shown in FIG. 7, includes end segment 110 configured to emit light. Gauge catheter 108 does not carry stent 10 and does not need to have a balloon. Gauge catheter 108 can have fiber optic wire 112 configured to deliver light and receive image signals. Fiber optic wire 112 can be coupled to camera 114 configured to provide an image taken from within the Eustachian tube. Gauge catheter 108 is introduced through the nasopharynx cavity and into the Eustachian tube to measure travel depth that is needed to place stent 10 at a desired distance away from the tympanic membrane. After the travel depth is determined, gauge catheter 108 is withdrawn from the Eustachian tube. Delivery catheter 100, which carries stent 10, will then be introduced through the nasopharynx cavity and into the Eustachian tube according to the pre-determined travel depth.

Figure 8:
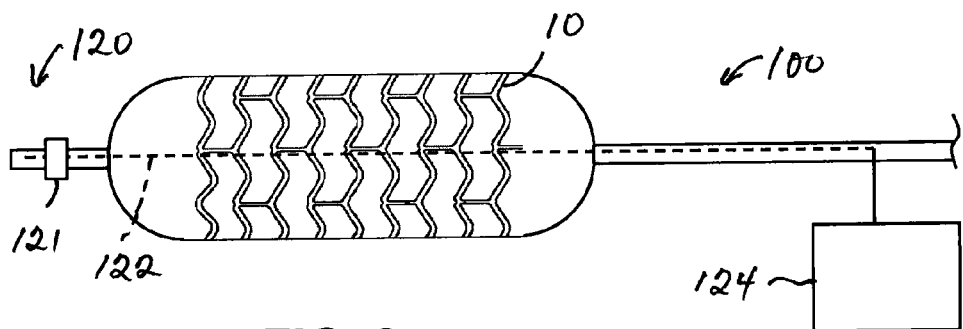
FIGS. 8 and 9 are plan views showing a stent on exemplary delivery catheters.

As shown in FIG. 8, delivery catheter 100, which carries stent 10, can include end segment 120 configured to emit light as a safety feature. Light coming from the tip of the catheter can be used to determine when the tip of delivery catheter 100 is near the tympanic membrane so that forward movement of delivery catheter 100 can be stopped to avoid contact with the tympanic membrane. In addition or alternatively, metallic band 121 can be attached to the catheter tip as a safety feature.

Figure 19:
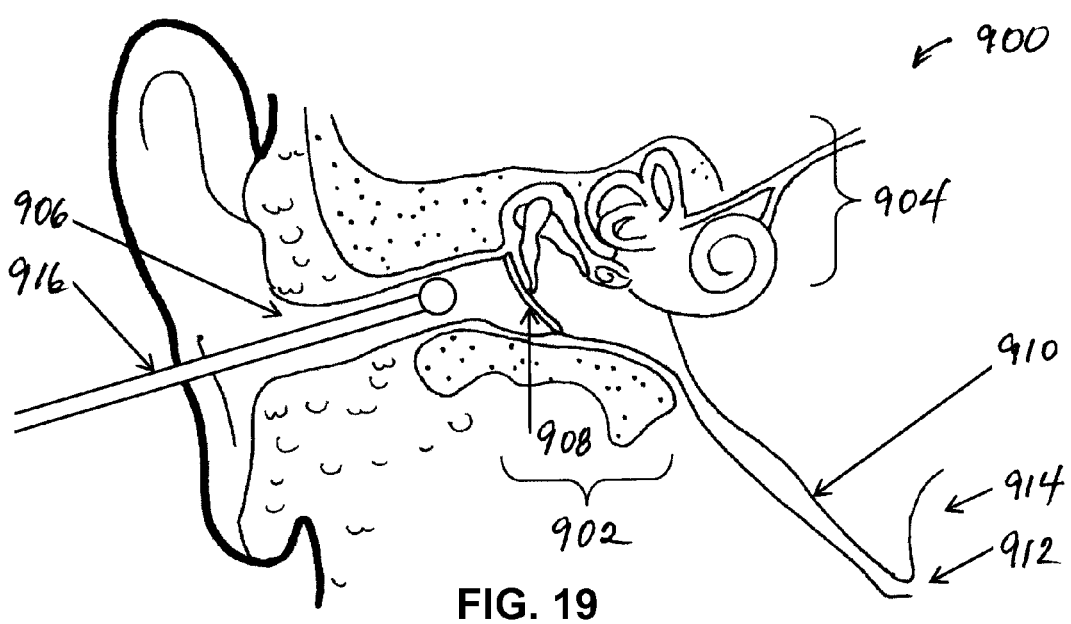
FIG. 19 is a section view showing a human ear and an exemplary probe placed in the ear canal.

For example, as shown in FIG. 19, probe 916 is located in the ear canal, on the other side of the tympanic membrane. Probe 916 can have a light sensor and/or a metal detector that detects light from the catheter tip and/or detects metal. When the light and/or metal is detected, the probe can generate an alarm that alerts a physician when forward movement of delivery catheter 100 should be stopped. For example, probe 916 can be configured such that it generates the alarm when the catheter tip has traversed through the Eustachian tube and has begun to enter the middle ear where the tympanic membrane is located.

In addition or alternatively, delivery catheter 100 can have fiber optic wire 122 configured to deliver light and receive image signals. Fiber optic wire 122 can be coupled to camera 124 configured to provide an image taken from within the Eustachian tube. The image is used to provide visual orientation of stent 10 during delivery of stent 10 into the Eustachian tube.

Figure 9:
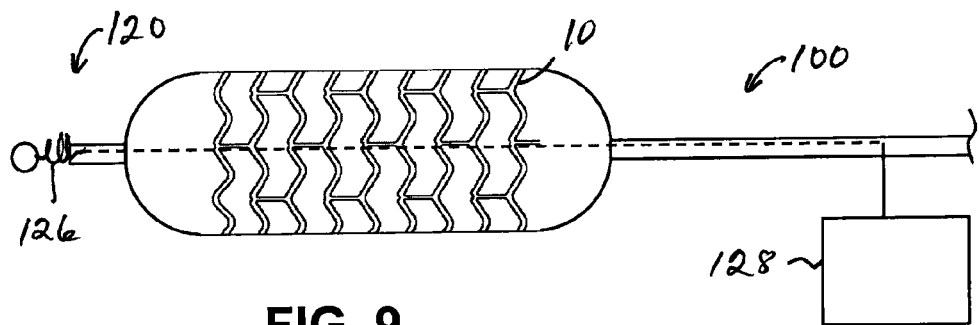

In addition or alternatively, end segment 120 of delivery catheter 100 can have soft, collapsible spring 126 coupled to indicator device 128, as shown in FIG. 9. Spring 126 is a safety feature that enables detection of when contact with tissue occurs. Upon tissue contact, spring 126 collapses to prevent damage to the tissue. The collapse of spring 126 is detected by indicator device 128 which generates an alarm that alerts a physician when forward movement of delivery catheter 100 should be stopped.

In some embodiments, end segment 110 of gauge catheter 108 has a soft, collapsible spring coupled to indicator device similar to that described for delivery catheter 100 in FIG. 9.

Figure 10:
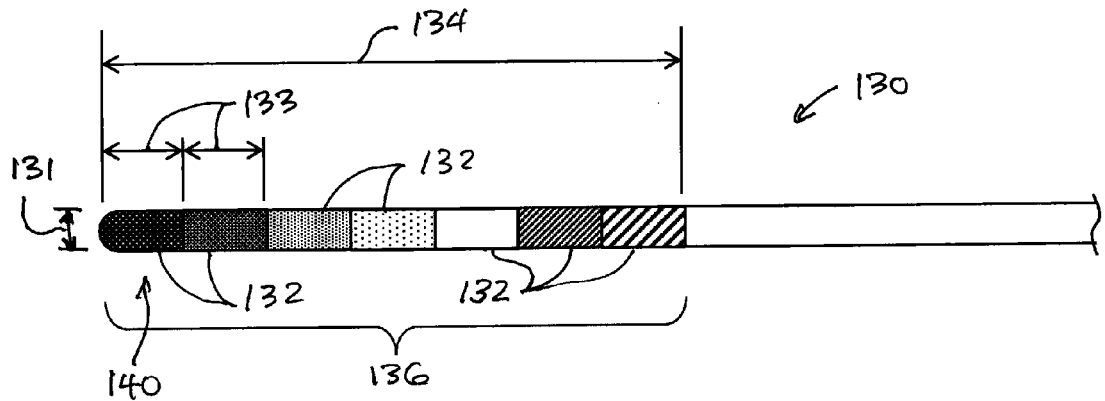
FIG. 10 is a plan view showing an exemplary guidewire for use in the Eustachian tube.

As shown in FIG. 10, exemplary guidewire 130 can be used to guide delivery catheter 100 into the Eustachian tube. Guidewire 130 can have an outer diameter 131 that is up to 1 mm, or about 1 mm. Guidewire 130 is sized to fit within internal passageway 105 within delivery catheter 100. Typically, guidewire 130 is placed within the Eustachian tube. Then guidewire 130 functions like a stationary track over which delivery catheter 100 travels. Delivery catheter 100 is pushed forward into the Eustachian tube as delivery catheter 100 slides over guidewire 130.

In some embodiments, guidewire 130 includes any one or a combination of the same safety features (e.g., light emitted from the tip, a metallic band, fiber optic wire and camera, and soft spring) that were described above for delivery catheter 100.

Guidewire 130 includes wire marks 132 visible on the surface of guidewire 130. Wire marks 132 are arranged periodically along full axial length 134 of end segment 136 of guidewire 130. In use, guidewire 130 would be placed in the Eustachian tube adjacent to or partially within an endoscope or other imaging device configured to take an image of end segment 136 in relation to surfaces of the Eustachian tube which surround end segment 136. Based on an image taken by the endoscope or other device from within the Eustachian tube, wire marks 132 would be used to determine the length of the treatment zone of the Eustachian tube. The overall length of the stent 10 can be selected to be about the same as the length of the treatment zone. For example, the length of the treatment zone may be determined to be about 15 mm, so stent 10 having overall length 21 that is about 15 mm may be selected. By determining the length of the treatment zone before stent deployment, it would be possible to select a stent having an overall length that is as small as possible in order to minimize the risk of interfering with the natural function of other portions of the Eustachian tube.

In FIG. 10, wire marks 132 are in the form of a connected series of bands having varying shades or varying colors that allow each wire mark 132 to be distinguished from adjacent wire mark 132. Each band encircles end segment 136. From an image taken by an imaging device (e.g., an endoscope) from within the Eustachian tube, the variations in shade or color can enable a physician to select a particular band within or adjacent the treatment zone. The selected band would be where end segment 120 of delivery catheter 100 would be placed prior to expansion of balloon 102 to deploy stent 10 in the Eustachian tube. The shade or color of the particular band selected by the physician allows for identification of the same band when delivery catheter 100 is being pushed over guidewire 130 while guidewire 130 remains stationary. Movement of delivery catheter 100 can be stopped when end segment 120 of delivery catheter 100 reaches the particular wire mark 132 (e.g., band) which was previously selected.

In the illustrated embodiment, wire marks 132 are in the form of bands of equal, pre-determined axial size 133 but of varying shades or varying colors that allow wire marks 132 to be distinguished from each other. With advance knowledge of the axial size of each band, a physician can gauge the length of the treatment zone of the Eustachian tube. For example, axial size 133 for all bands can be the same axial dimension. That axial dimension can be from 1 mm to 5 mm, from 1 mm to 4 mm, from 1 mm to 2 mm, from 1 mm to 2 mm, about 2 mm, or about 1 mm. In alternative embodiments, the bands can be unequal in axial dimension.

Wire marks 132 can be exclusively present in end segment 136. The remaining segment of guidewire 130 need not have any of the wire marks. Full axial length 134, in which wire marks 132 are present, can be at least as long as the Eustachian tube. For example, full axial length 134 of end segment 136 can be from 35 mm to 65 mm, or from 35 mm to 45 mm, or about 35 mm.

Wire marks 132 can include a thin material that is applied on the surface of guidewire 130. Wire marks 132 can be applied by a printing process, a painting process, or an adhesive. The thin material can have a color that contrasts with areas of guidewire 130 which surround wire marks 132. Additionally or alternatively, wire marks 132 can include an etched mark on the surface of guidewire 130. The etched mark, which can be produced by a laser or other method, can be opaque and have a level of opacity that makes it readily visible and distinguishable from areas of guidewire 130 which surround wire marks 132. Additionally or alternatively, each wire mark 132 can have a color or opacity that distinguishes the wire mark from adjacent wire marks. Additionally or alternatively, each wire mark 132 can have a shape (such as a circle, square, rectangle, alphanumeric character, or combination thereof) that distinguishes the wire mark from adjacent wire marks. Additionally or alternatively, wire marks 132 can be periodically arranged so that all the wire marks are equally spaced apart from each other. Additionally or alternatively, wire marks 132 can be periodically arranged so that at least some of the wire marks are equal in size and abut each other.

Figure 11:
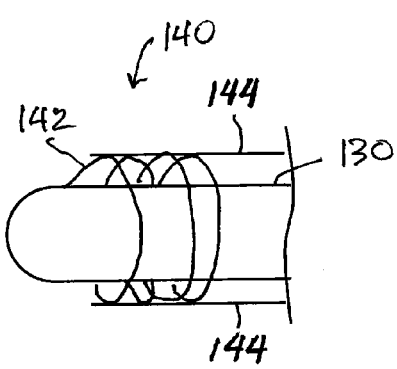
FIGS. 11 and 12 are partial section views showing exemplary end segments of a guidewire.
Figure 12:
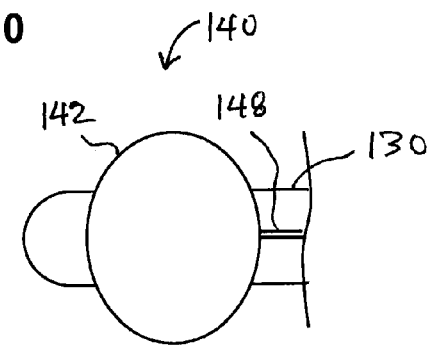

As shown in FIGS. 11 to 12, guidewire end segment 140 of guidewire 130 can include a stabilization feature 142. Stabilization feature 142 can be present on guidewire 130 having the wire marks described above.

In FIG. 11, exemplary stabilization feature 142 is in the form of a compressed spring which is confined within tubular sheath 144. Spring 142 can be made of a superelastic nickel-titanium alloy, such as Nitinol, or other elastic material. Guidewire 130 and sheath 144 are pushed forward together into the Eustachian tube. When guidewire end segment 140 has reached a desired location in the Eustachian tube (such the bony segment or a location beyond a treatment zone), sheath 144 is pulled backwards away from guidewire end segment 140, which allows spring 142 to expand and engage the surrounding surface of the Eustachian tube. When expanded, spring 142 prevents or inhibits subsequent axial movement of guidewire 130. Next, stent 10 can be implanted according to processes previously described for tracking delivery catheter 100 over guidewire 130.

In FIG. 12, exemplary stabilization feature 142 is in the form of an inflatable balloon. Guidewire 130 is pushed forward into the Eustachian tube while inflatable balloon 142 is deflated. When guidewire end segment 140 has reached a desired location in the Eustachian tube (such the bony segment or a location beyond a treatment zone), balloon 142 is inflated and expands by introduction of fluid through fluid passageway 148 in guidewire 130. The inflated balloon engages the surrounding surface of the Eustachian tube and prevents or inhibits subsequent axial movement of guidewire 130. Next, stent 10 can be implanted according to processes previously described for tracking delivery catheter 100 over guidewire 130.

As shown in FIG. 13, polymer substrate 150 of one or more rings 12 is optionally covered by coating 152. FIG. 13 is a cross-section view in a radial direction that is perpendicular to central axis 50 of the stent. Stent coating 152 can be applied on substrate 150 by spraying, immersion, or other method. Stent coating 152 is applied on abluminal surface 154 and luminal surface 156 of substrate. The term "abluminal surface" refers to the radially outward facing surface or the surface that faces away from central axis 50 of stent 10. The term "luminal surface" refers to the radially inward facing surface or the surface that faces toward central axis 50 of stent 10. In alternative embodiments, stent coating 152 can be present on abluminal surface 154 but not on luminal surface 156 when it is desired to deliver a drug or other therapeutic agent directly to inner surfaces of the Eustachian tube.

In some embodiments, stent coating 152 is a polymer without any drug or other therapeutic agent. In alternative embodiments, stent coating 152 is a combination of a polymer and a therapeutic agent. For example, the therapeutic agent can be everolimus. The therapeutic agent can be an antihistamine, an anti-inflammatory steroid, an antibiotic, a corticosteroid, or other type of therapeutic agent. An antihistamine can inhibit mucous build up that can clog the Eustachian tube. The polymer can be polylactide (PLA) or a polymer based on PLA. Forms of PLA include poly-L-lactide (PLLA) and poly-D-lactide (PDLA). Polymers based on PLA include graft copolymers, block copolymers, such as AB block-copolymers ("diblock-copolymers") or ABA block-copolymers ("triblock-copolymers"), and mixtures thereof.

Polymer substrate 150 can be a bioresorbable material. The polymer substrate material can be polylactide (PLA) or a polymer based on PLA, as was described above for stent coating 152. Examples of materials for polymer substrate 150 include without limitation poly(lactic-co-glycolic acid) (PLGA), poly(glycolic acid), poly(glycolide) (PGA), poly (L-lactic acid), poly(L-lactide) (PLLA), poly(D,L-lactic acid), and poly(caprolactone) (PCL) copolymers. As a further example, polymer substrate 150 can be made from a PLLA/PCL copolymer.

Polymer substrate 150 can be a biostable material. Example materials for a biostable polymer substrate include without limitation polyurethanes (SPU), polypropylene (PP), and polyetherimide block copolymers (e.g., PEBAX (R)).

As discussed above, the polymer substrate of stent 10 can be coated with a therapeutic agent. Additionally or alternatively, polymer substrate 150 can incorporate a therapeutic agent. The location of the therapeutic agent (whether in polymer substrate 150 and/or stent coating 152) can be controlled such that the drug is present on the portion of stent 10 that will be in the cartilaginous segment of the Eustachian tube. For example, the therapeutic agent can be located within proximal segment 22 but not distal segment 24. As a further example, the therapeutic agent can be located within proximal segment 22 and distal segment 24 if both of these segments will be implanted within the cartilaginous segment of the Eustachian tube.

As discussed above, a stent can be implanted within the Eustachian tube to deliver a therapeutic agent. A coating on a balloon can also be used to deliver a therapeutic agent to the Eustachian tube or a sinus cavity.

Balloon 102 of delivery catheter 100 can be coated with any of the previously mentioned therapeutic agents for stent 10. Balloon 102 can have coating 206 as described below.

Figure 14:
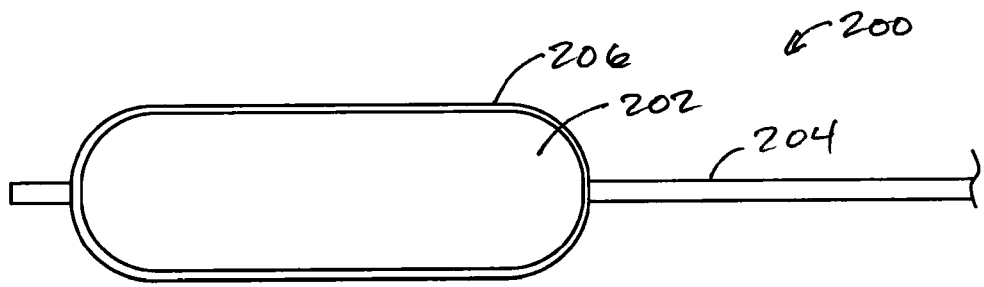
FIGS. 14-16 are partial section views showing exemplary coated balloon catheters that can be used to carry stent.

In FIG. 14, coated balloon catheter 200 includes balloon 202 at the end of catheter body 204. Balloon coating 206 has been applied onto the balloon substrate material, such as by spraying, immersion, or other method. Balloon coating 206 includes a therapeutic agent, such that balloon coating 206 can be the therapeutic agent without a polymer carrier or balloon coating 206 can be a combination of the therapeutic agent and a polymer carrier. As used herein, a polymer carrier is a matrix in which a therapeutic agent is blended or carried. Balloon 202 can be inflated to deliver a therapeutic agent without there being a stent on balloon 202. Alternatively, balloon 202 can be inflated to deliver a therapeutic agent while a stent (such as stent 10 described above) is deployed by balloon 202.

Balloon coating 206 can be configured for any of (1) homogenous transfer of a therapeutic agent to the entire sinus wall or the entire treatment zone within Eustachian tube, (2) rapid release of high concentrations of a therapeutic agent at the sinus wall or Eustachian tube, and (3) controlled release of the therapeutic agent for predetermined periods of time with little impact on long-term healing.

In some embodiments, coated balloon 206 is configured for insertion into the sinus to provide sinus dilation. Sinus dilation can be performed alone or in combination with conventional sinus surgery techniques as part of a functional endoscopic sinus surgery (FESS) procedure. For some patients, balloon sinus dilation may be an effective alternative to conventional sinus surgery. Balloon sinus dilation can be an in-office procedure performed under local anesthesia, in which coated balloon 206 is used to reshape the sinus and nasal drainage pathway anatomy and thereby deliver instant relief that lasts. Patients can return to normal activity within forty-eight hours after the balloon sinus dilation procedure.

Balloon coating 206 can be any therapeutic agent without a polymer carrier. The therapeutic agent can be any of those mentioned or referred to below. Absence of a polymer in balloon coating 206 may decrease chronic inflammation. Absence of a polymer carrier can be accomplished by applying the therapeutic agent directly to the balloon substrate material. This can also be accomplished by dissolving or dispersing the therapeutic agent in solvent or other liquid, and then applying the resulting solution or mixture onto the balloon substrate material. Thereafter, the solvent or other liquid is allowed to evaporate and leave the therapeutic agent on the balloon substrate.

Balloon coating 206 can be combination of any therapeutic agent mentioned or referred to below and any polymer material mentioned or referred to below. Such combination can be created by dissolving or suspending the therapeutic agent in the polymer. Any polymer known to be suitable for coating an inflatable balloon can be used. Examples of polymers include polyvinylpyrrolidone (PVP) and other water soluble polymers, such as hydrogels.

In some embodiments, the therapeutic agent is a hydrophobic drug that reduces inflammation in the sinus or the Eustachian tube. Examples of such therapeutic agents include without limitation mometasone furoate, dexamethasone, paclitaxel, and a derivative of paclitaxel.

In some embodiments, the therapeutic agent is an anti-inflammatory drug and a hydrophobic antibiotic. A non-limiting example of an antibiotic is doxycycline.

As used herein, the term "nanoparticle" encompasses coarse, fine, and ultrafine nanoparticles. A nanoparticle can have a diameter between 2,500 and 10,000 nanometers (for coarse nanoparticles), between 100 and 2,500 nanometers (for fine nanoparticles), or between 1 and 100 nanometers (for ultrafine nanoparticles).

In some embodiments, the therapeutic agent is encapsulated within a nanoparticle or microparticle. Then, the nanoparticles or microparticles are applied on the balloon substrate. The nanoparticle or microparticle can be a polymeric nanoparticle or polymeric microparticle.

Figure 17:
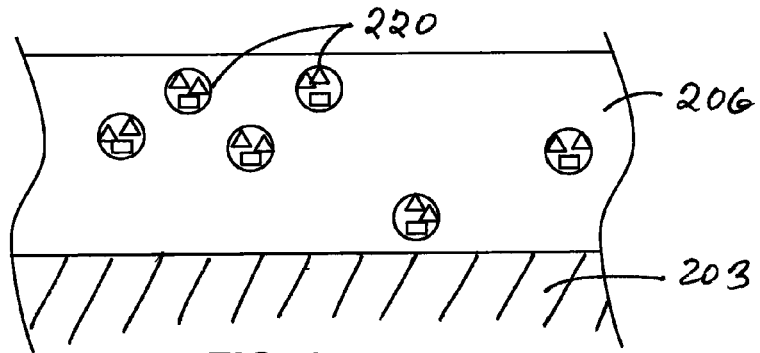
FIGS. 17 and 18 are schematic views showing exemplary coatings for coated balloon catheters.

For example, as shown in FIG. 17, balloon coating 206 can include polymeric nanoparticles 220, which is schematically represented by a circle. Each nanoparticle encapsulates an antibiotic (e.g., doxycycline, other tetracycline antibiotic, ciproflaxin, or other quinolone antibiotic) schematically represented as a triangle, and another therapeutic agent (e.g., mometasone furoate, dexamethasone, other corticosteroid, paclitaxel, a derivative of paclitaxel other substance used for stent coating 152, or another anti-inflammatory substance) schematically represented as a rectangle. The antibiotic and the other therapeutic agent can be present in a predetermined ratio within each polymeric nanoparticle. For example, the ratio of antibiotic to the other therapeutic agent can be 2:1, as indicated in FIG. 17. Other ratios are possible. Balloon coating 206 optionally includes a polymer which carries nanoparticles 220.

Figure 18:
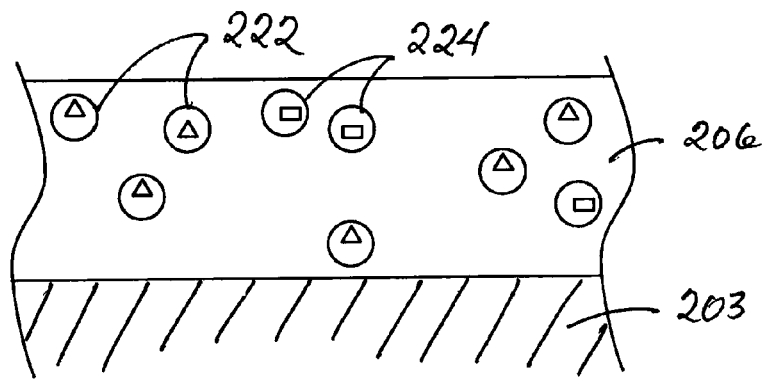

As a further example, as shown in FIG. 18, balloon coating 206 can include polymeric nanoparticles in which a first group 222 of the nanoparticles encapsulate an antibiotic (schematically represented as a triangle) and a second group 224 of the nanoparticles encapsulate an anti-inflammatory or other therapeutic agent (schematically represented as a rectangle). The first group of nanoparticles is mixed with the second group of nanoparticles at a predetermined ratio, and then the mixture of nanoparticles is applied to balloon wall 203. For example, the ratio of the first group of nanoparticles (containing an antibiotic) to the second group of nanoparticles (containing an anti-inflammatory or other therapeutic agent) can be 2:1, as indicated in FIG. 18. Other ratios are possible. Balloon coating 206 optionally includes a polymer which carries the nanoparticles.

In some embodiments, the nanoparticles which encapsulate an antibiotic are polyanhydride nanoparticles containing ciprofloxacin as the antibiotic. The polyanhydride nanoparticles would allow for relatively fast degradation.

In some embodiments, the nanoparticles containing ciprofloxacin or other antibiotic are blended with a composition of poly(caprolactone-co-glycolide) (PCL-co-PGA) or other bioresorbable polymer matrix. To form balloon coating 206, the blend can be mounted on balloon wall 203 as a flat ribbon. When balloon 202 is expanded in a cavity, the flat ribbon will be warmed to a temperature from about 40 to about 50 degrees C. and paved in situ in the Eustachian tube as a drug-carrying and load-bearing transient liner. Warming can be achieved by inflating the balloon with a fluid that has been warmed to a temperature from about 40 to about 50 degrees C. Balloon coating 206 (in the form of the ribbon) reshapes and conforms to the surface of the Eustachian tube. As an alternative to heating, the blend can include dimethyl sulfoxide (DMSO) which would allow for paving and reshaping of the ribbon when balloon 202 is expanded.

In some embodiments, any therapeutic substances listed herein can be encapsulated in a particle, then the particles blended with a composition of poly(caprolactone-co-glycolide), and then the blend can be applied to form balloon coating 206. The blend can optionally include DMSO.

In some embodiments, the therapeutic agent is itself a nanoparticle, such as a nanocrystal. For example, balloon coating 206 can include a mixture of nanocrystals of an antibiotic and nanocrystals of another therapeutic agent selected from the examples mentioned above or other anti-inflammatory substances.

In some embodiments, particle formulation of the antibiotic in balloon coating 206 is selected to provide the most appropriate duration of release. For example, the nanoparticles can be formulated such that an antibiotic is released from the nanoparticles over a period of 2 to 7 days, or about 7 days. Also, particle formulation of the other therapeutic agent in balloon coating 206 is selected to provide the most appropriate duration of its release. For example, the nanoparticles can be formulated such that another therapeutic agent, such as an anti-inflammatory substance, can be released over a period of greater than 7 days, greater than 14 days, or about 14 days to about 28 days.

For example, the nanoparticles can be made of a bioresorbable polymer in the size ranges of 75 um to 1000 um. The bioresorbable polymer can be for example, without limitation, PLLA, poly(D,L-lactic acid), or PLGA. The molecular weight of the polymer, drug-polymer miscibility governed by polymer type and drug type, polymer equilibrium water uptake, and the size of the polymer will dictate the release rate of the drug. These parameters can be adjusted to obtain 80% drug release in a range of periods from 3 days up to 180 days.

Structural patterns on balloon 202 can be varied for Eustachian tube access to allow for differences in mechanical properties in different segments of the Eustachian tube. As previously discussed, the forward segment (nearest the tympanic membrane) of the Eustachian tube is bony, and the rear segment (nearest the opening) of the Eustachian tube is cartilaginous. Balloon 202 can be configured to exert greater expansionary force at a forward segment of the balloon if the forward segment will be placed in the bony segment of the Eustachian tube.

Balloon 202 can have a length-dependent compliance. As used herein, the term "compliance" refers to the ability of the balloon 202 to collapse in response to external pressure applied to the balloon. When balloon rear segment 210 is intended to be inflated in the cartilaginous segment, balloon rear segment 210 is configured to have a compliance that is greater than that of balloon forward segment 208. The greater compliance of balloon rear segment 210 can allow for natural collapse and closing of the cartilaginous segment of the Eustachian tube.

Figure 15:
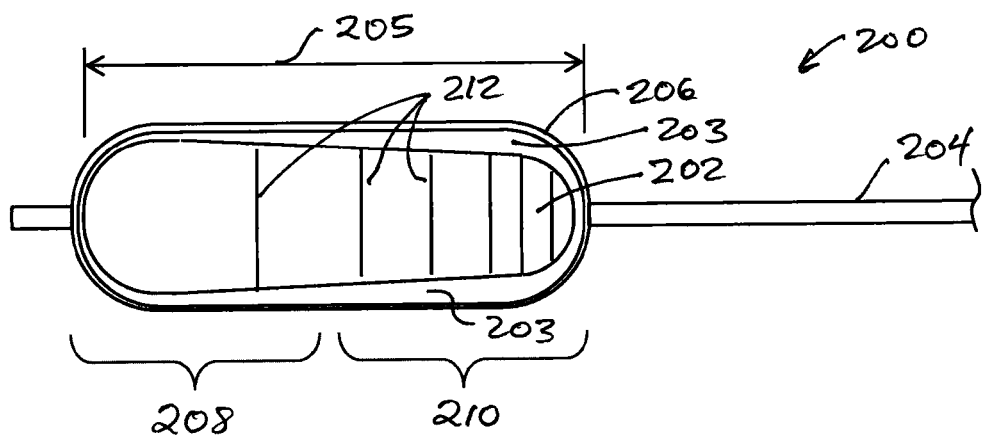

As shown in FIG. 15, exemplary balloon 202 includes balloon forward segment 208 and balloon rear segment 210. Balloon forward segment 208 can be configured to exert greater expansionary (radially outward) force to surrounding tissue (such as the bony segment of the Eustachian tube) as compared to balloon rear segment 210. The interior of balloon 202 can include ribs 212 which can limit expansion of balloon 202. Balloon rear segment 210 can have a greater number of ribs 212 than balloon forward segment 208. The greater number of ribs 216 can reduce the ability of balloon rear segment 210 to expand as compared to balloon forward segment 208. In addition or alternatively, the thickness of wall 203 of balloon 202 can be thicker at balloon rear segment 210 as compared to balloon forward segment 208. The thicker wall of balloon rear segment 210 can reduce the ability of balloon rear segment 210 to expand.

Figure 16:
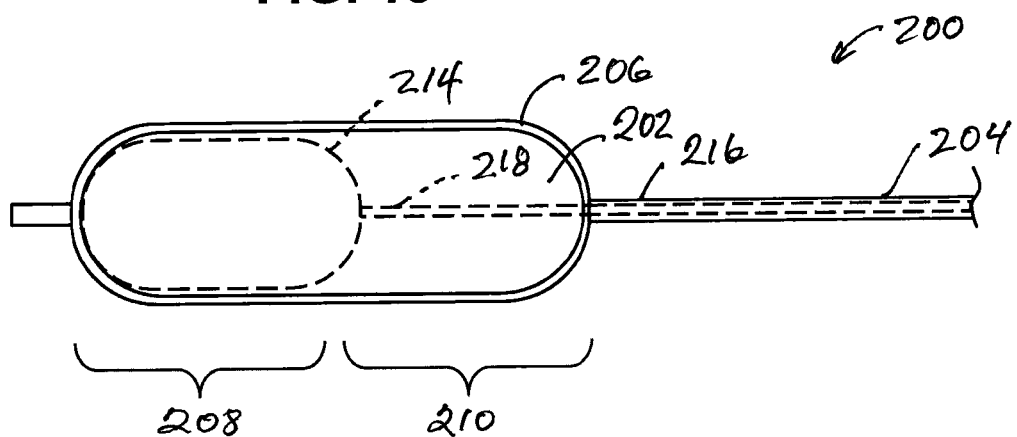

As shown in FIG. 16, exemplary balloon 202 includes inner balloon 214 at balloon forward segment 208. Balloon 202 is inflated by fluid introduced through first fluid passageway 216, and inner balloon 214 is inflated by fluid introduced through second fluid passageway 218 Inner balloon 214 is inflated at a greater fluid pressure than the remainder of balloon 202. Greater fluid pressure at balloon forward segment 208 allows for greater expansionary (radially outward) force to surrounding tissue (such as the bony segment of the Eustachian tube) as compared to balloon rear segment 210. A lower fluid pressure in balloon rear segment 210 results in greater compliance at balloon rear segment 210, which can allow natural collapse and closing of the cartilaginous segment of the Eustachian tube. Optionally, the ribs and/or variable wall thickness described in FIG. 15 are implemented in coated balloon catheter 200 of FIG. 16.

In FIGS. 15 and 16, balloon forward and rear segments 208 and 210 appear to be about the same in axial length. In other embodiments, forward and rear segments 208 and 210 are unequal in axial length. For example, balloon forward segment 208 can be a percentage of overall axial length 205 of balloon 202, where the percentage can be from 10% to 50%, from 20% to 40%, or about 30%. Balloon rear segment 210 corresponds to the remaining percentage.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A polymeric stent for treating the Eustachian tube, the stent comprising:
a tubular scaffold configured for implantation in the Eustachian tube, the tubular scaffold having a polymer substrate, the tubular scaffold including a proximal segment and a distal segment, the proximal segment including radially deformable rings, the radially deformable rings of the distal segment having a greater radial strength than the radially deformable rings of the proximal segment, wherein the tubular scaffold has an uncrimped configuration and a crimped configuration, wherein the scaffold is cut from a frustoconical tube so that in the uncrimped state a diameter of the rings decreases linearly from a distal end to a proximal end of the scaffold, wherein the proximal segment begins at an end ring at the proximal end of the tubular scaffold and the distal segment begins at an end ring at the distal end of the tubular scaffold, wherein the proximal segment abuts the distal segment.

2. The polymeric stent of claim 1, wherein discontinuities are present in the radially deformable rings of the proximal segment, each of the discontinuities are defined as a cut through a full width and a full thickness of the radially deformable ring in which the discontinuity is present, and discontinuities are absent from the radially deformable rings of the distal segment.

3. The polymeric stent of claim 1, wherein one or more of the radially deformable rings of the distal segment have polymer molecules that have a preferential orientation that is less axial than that of the radially deformable rings of the proximal segment.

4. The polymeric stent of claim 1, wherein one or more of the radially deformable rings of the distal segment have full widths that are greater than that of one or more of the radially deformable rings of the proximal segment.

5. The polymeric stent of claim 1, wherein one or more of the radially deformable rings of the distal segment have full thicknesses that are greater than that of one or more of the radially deformable rings of the proximal segment.

6. The polymeric stent of claim 1, wherein the polymer substrate of one or more of the radially deformable rings of the distal segment has a molecular weight greater than that of the polymer substrate of one or more of the radially deformable rings of the proximal segment.

7. The polymeric stent of claim 1, wherein the polymer substrate includes a base component and a dopant having a lower elastic modulus than that of the base component, the base component is present at a higher percentage than the dopant in the polymer substrate of the radially deformable rings of the distal segment, and the dopant is present at a higher percentage than the base component in the polymer substrate of the radially deformable rings of the proximal segment.

8. The polymeric stent of claim 1, wherein the polymer substrate of one or more radially deformable rings of the distal segment has at least one parameter greater than that of the polymer substrate of one or more radially deformable rings of the proximal segment, the at least one parameter being any one or more of: melt temperature, glass transition temperature, and percent crystallinity.

9. The polymeric stent of claim 1, wherein one or more of the radially deformable rings of the distal segment have outer diameters that are greater than that of one or more of the radially deformable rings of the proximal segment.

10. The polymeric stent of claim 1, wherein the tubular scaffold includes a plurality of stent marks, the stent marks are spaced equally apart from each other, and each of the stent marks has a characteristic that differentiates the stent mark from a portion of the tubular scaffold that is adjacent to the stent mark, and the characteristic is an opacity, a color, a shade, a shape, an alphanumeric character, or a combination thereof.

11. The polymeric stent of claim 1, wherein a wall thickness of the frustoconical tube decreases between the distal end to the proximal end so that a thickness of the rings decreases from the distal end to the proximal end.

\* \* \* \* \*